(12) United States Patent  
Broome et al.

(10) Patent No.: US 10,458,988 B2
(45) Date of Patent: Oct. 29, 2019

(54) BIOTINYLATED LUMINESCENT PROBE

(71) Applicant: MUSC FOUNDATION FOR RESEARCH DEVELOPMENT, Charleston, SC (US)

(72) Inventors: Ann-Marie Broome, Charleston, SC (US); Yu-Lin Jiang, Charleston, SC (US)

(73) Assignee: MUSC Foundation for Research Development, Charleston, SC (US)

( * ) Notice: Subject to any disclaimer, the term of this patent is extended or adjusted under 35 U.S.C. 154(b) by 0 days.

(21) Appl. No.: 15/909,020

(22) Filed: Mar. 1, 2018

(65) Prior Publication Data

US 2018/0252718 A1    Sep. 6, 2018

Related U.S. Application Data

(60) Provisional application No. 62/466,617, filed on Mar. 3, 2017.

(51) Int. Cl.
*G01N 33/574* (2006.01)
*C07D 495/04* (2006.01)

(52) U.S. Cl.
CPC ......... *G01N 33/574* (2013.01); *C07D 495/04* (2013.01); *G01N 33/57407* (2013.01); *G01N 33/57492* (2013.01)

(58) Field of Classification Search
CPC ........................... C07D 495/04; G01N 33/574
See application file for complete search history.

(56) References Cited

U.S. PATENT DOCUMENTS

| 9,551,705 B2 * | 1/2017 | Hitko | ............... G01N 33/54326 |
| 10,168,323 B2 * | 1/2019 | Hitko | ................. G01N 33/543 |

* cited by examiner

*Primary Examiner* — Golam M Shameem

(57) ABSTRACT

Provided herein are luminescent probes of formula I:

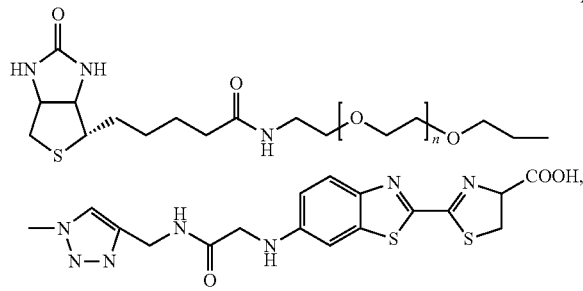

and complexes thereof for the detection of cancer cells.

8 Claims, 3 Drawing Sheets

BIOTINYLATED LUMINESCENT PROBE

FIELD OF THE INVENTION

The invention is directed to a water-soluble, biotinylated bioluminescent probe. The probe is useful for the detection of, for example, cancer cells.

All publications, patents, patent applications, and other references cited in this application are incorporated herein by reference in their entirety for all purposes and to the same extent as if each individual publication, patent, patent application or other reference was specifically and individually indicated to be incorporated by reference in its entirety for all purposes. Citation of a reference herein shall not be construed as an admission that such is prior art to the present invention.

BACKGROUND OF THE INVENTION

Imaging has become one of most important techniques in identifying and monitoring cancer in non-invasive diagnosis as well as in accurate surgical resection during treatment. First, it is crucial to detect tumor cells at an early stage of development. The most commonly used methods for detecting cancer in patients include magnetic resonance imaging (MRI), computerized tomography (CT), and positron-emission tomography (PET). Second, cancer treatments can include surgical resection, chemotherapy, and radiation. Surgery is one of the most effective ways to remove tumors and avoid metastatic disease spread. Surgery cures approximately 45% of all cancer patients with solid tumors. To be considered successful, a surgeon must remove the entire tumor and any lymph nodes or satellite nodules containing tumor cells. Partial removal of the solid tumor and incomplete removal of all the tumor cells decrease a patient's survival rate by 5-fold. Therefore, it is important to map the solid tumor accurately using imaging before surgery and double check for any residual tumor cells during and after surgery.

Recently, fluorescence imaging has been suggested for use in both cancer detection and resection; however, it is a light-dependent method. Fluorescence imaging requires an external light source to excite exogenously-added fluorescence agents and is not very versatile due to the fact that many biological molecules present in the body have significant absorption of wavelengths at both visible and infrared regions of the light spectrum. Further, many wavelengths generated from the external, excitation light source cannot penetrate tissues to reach the imaging fluorescent molecules, especially when they are in solid tumors. When the fluorescent molecules are not excited, no light is emitted for detection of the cancer. To overcome this problem, luminescence imaging is being developed to emit light from within the solid tumor. The process involves an enzyme, such as luciferase, which catalyzes the oxidation of a substrate, i.e., luciferin, to generate a bioluminescent signal, which is measurable by photon emission. Light is generated without application of an external excitation light source. The enzymatically-generated photons are able to travel through solid tumors during the detection process.

Although humans and animal models of cancer do not have naturally occurring bioluminescent genes, such as luciferase, the genes or proteins can be introduced for imaging purposes. For instance, bacteria encoded with a luciferase gene can accumulate in C6 glioma tumors in a mouse model. The expressed luciferase is then used for cancer detection in vivo. Furthermore, mammalian cells genetically modified with a luciferase gene can be delivered directly into tumors in live animals for tumor detection using bioluminescence.

In addition, tumor bioluminescence can be a useful tool during surgery as shown in an animal model. Bioluminescence was able to precisely detect both tumors preoperatively and intra-operatively. For the enzyme to produce bioluminescence within the tumor, D-luciferin or other small molecule substrates, such as coelenterazine, vargulin, and 6-aminoluciferin derivatives, must be administered. However, bioluminescence generated from these substrates lasts for a very short time—only 15 to 20 minutes per administration. This is not practical in a clinical setting as the surgery to remove a brain tumor takes 3 to 5 hours. Checking and re-checking for tumor remnants by bioluminescence would require multiple new administrations of substrate. The additional application steps would lengthen the surgical time and potentially complicate the surgery and reduce the success rate of the surgery. Therefore, a new substrate with longer lasting bioluminescence signal is needed.

A need, therefore, exists in the art for new probes for the detection of cancer cells.

SUMMARY OF THE INVENTION

The present invention is directed to a bioluminescent probe of formula I:

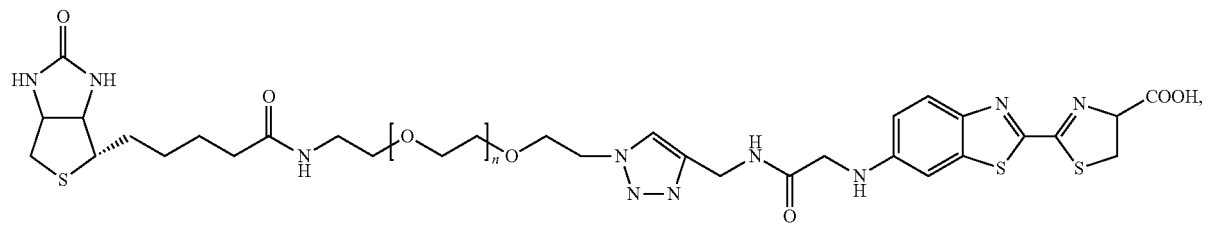

I wherein n is 10 to 200, and complexes thereof with, for example, streptavidin or avidin; and assays, methods and kits for detecting cancer in a sample.

DETAILED DESCRIPTION OF THE INVENTION

Figure 1:
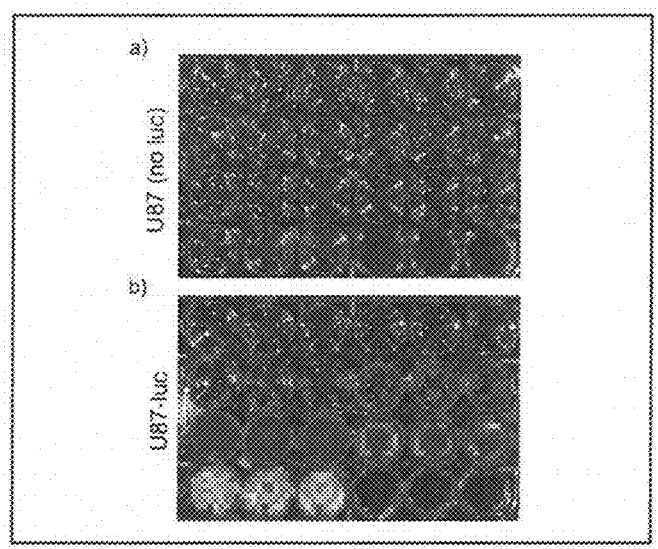
FIG. 1 shows a B-YL substrate useful to identify enzymatic activity in brain tumor cell lines transfected with luciferase. Triplicate wells were plated with increasing numbers of either U87 cells without luciferase (a) or with luciferase (b). In each plate: Row 1, wells 1-3, no cells; wells 4-6, 1,875 cells per well. Row 2, wells 1-3, 3,750 cells per well; wells 4-6, 7,500 cells per well. Row 3, wells 1-3, 15,000 cells per well; wells 4-6, 30,000 cells per well. Row 4, wells 1-3, 60,000 cells per well. Incubation buffer, Leibovitz's L-15 medium with $MgCl_2$ (5 mM). Each well was incubated with B-YL (100 μg/mL). Plates were imaged using an IVIS 200 In vivo Imaging System. Escalating luminescence was observed only in wells containing luciferase-expressing cells (b). No luminescence was observed in cells lacking luciferase (a).

It is to be understood that the terminology employed herein is for the purpose of describing particular embodiments, and is not intended to be limiting. Further, although any methods, devices and materials similar or equivalent to those described herein can be used in the practice or testing of the invention, certain embodiments of such methods, devices and materials are now described The invention is directed to, for example, a novel biotin containing bioluminescent probe herein referred to as B-YL, which acts as a substrate for luciferase was synthesized. In one embodiment, n is 10 to 200. In another embodiment, n is 10 to 150. In a further embodiment, n is 10 to 100. In a still further embodiment, n is 10 to 50. In certain embodiments, n is 11, 23, 45 or 114. In certain embodiments, the value of n is dependent upon the PEG length desired, such as PEG 500, 2000 or 5000.

The probe possesses an aminoluciferin unit as a bioluminescent reporter, a polyethylene glycol link, for example, PEG-1000, for improving cell penetrating ability, and a biotin tail for binding to streptavidin or avidin. A complex can be constructed comprising streptavidin (SA) or avidin, the bioluminescent probe B-YL, and a biotinylated epidermal growth factor short peptide (B-EGF) (SA/B-YL/B-EGF=1/3/1, molar ratio) to target the complex. The EGF peptide binds to the EGF receptor, a biomarker overexpressed in 30-50% of high-grade gliomas. The complex can be used, for example, to detect implanted brain tumor cells encoded with the luciferase gene by bioluminescence in vitro and in vivo.

Thus, the compound of the invention can be used, for example, to target enzyme substrates in the far-red spectral region for non-invasive imaging of cells through, for example, fluorescence microscopy, confocal microscopy or in vivo fluorescence imaging. At the microscopy level, the product could be used after characterization with fluorescence efficiency and cell viability assays. For in vivo use, the probe of the invention would be useful with, for example, analysis of biodistribution and pharmacodynamic evaluation of degradation products.

Compounds of the present invention can be prepared beginning with commercially available starting materials and utilizing general synthetic techniques and procedures known to those skilled in the art. For example, the compounds of the invention can be prepared according to the below schemes.

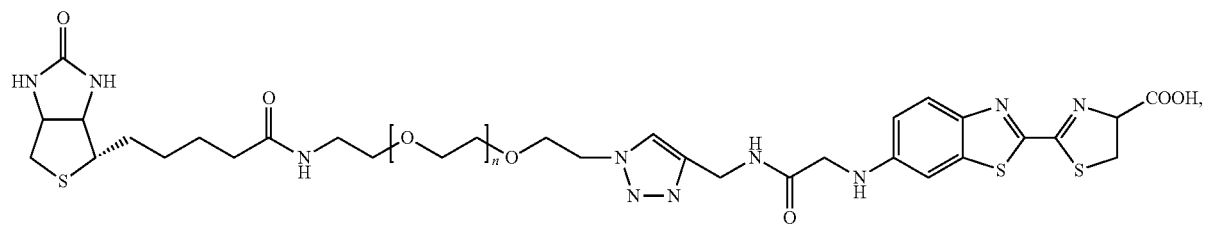

Scheme 1. Synthesis of Probe B-YL (1).

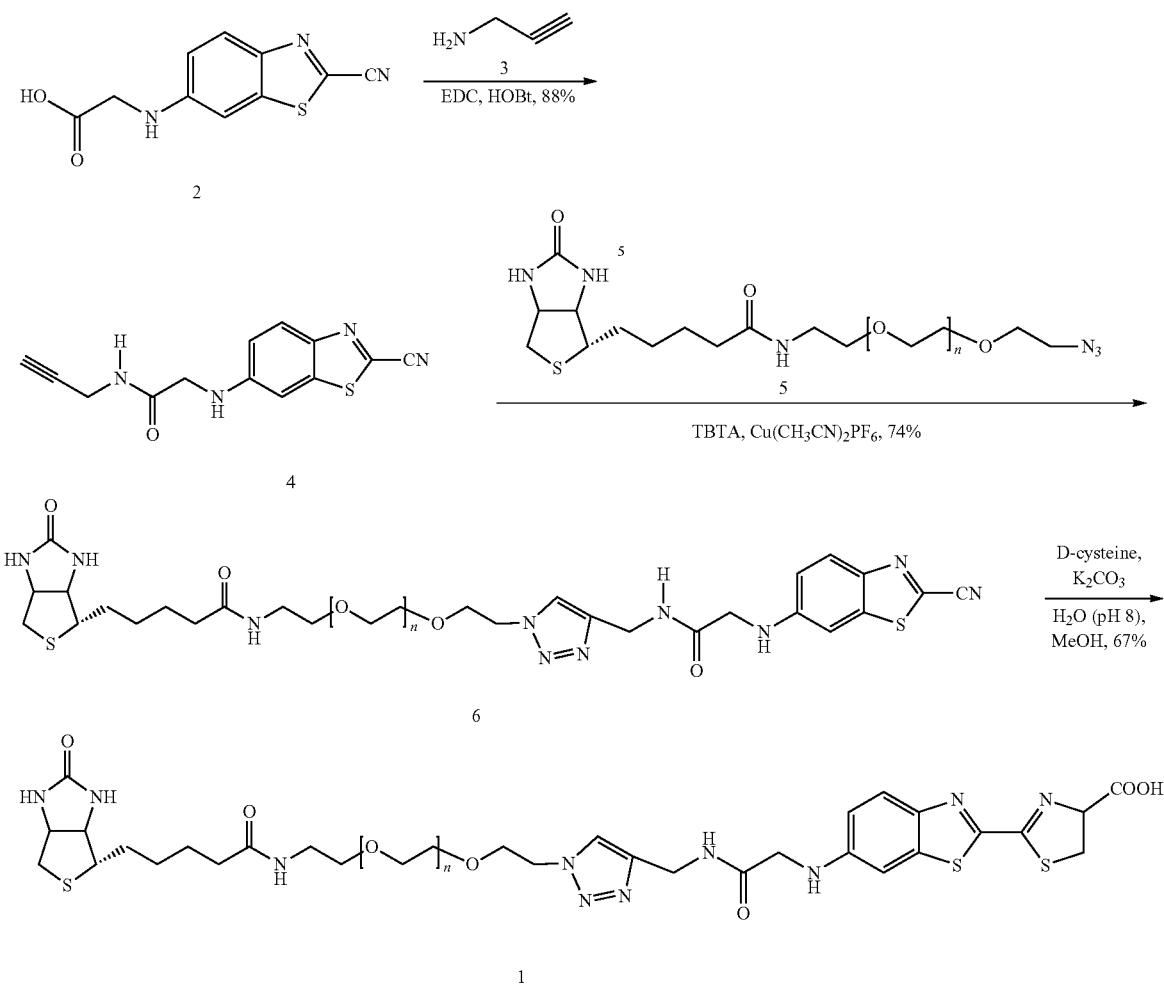

The synthesis of substrate B-YL is outlined in Scheme 1. Synthesis can begin with compound 2. Compound 2 can be amidated with propargylamine (3) in the presence of 1-ethyl-3-(3-dimethylaminopropyl)-carbodiimide (EDC) and 1-hydroxy-benzotriazole (HOBt), resulting in compound 4 (88% yield). The latter can be reacted with biotinylated azidoPEG (5) by Click chemistry in the presence of $Cu(CH_3CN)_2PF_6$ and tris-[(1-benzyl-1H-1,2,3-triazol-4-yl)methyl]amine (TBTA), affording compound 6 (74% yield). Finally, compound 6 can be reacted with D-cysteine in the presence of $K_2CO_3$ at pH 8.5 to produce probe B-YL (1) in 67% yield.

The synthesis of azidoPEG (S), a new and useful synthetic intermediate, is shown below:

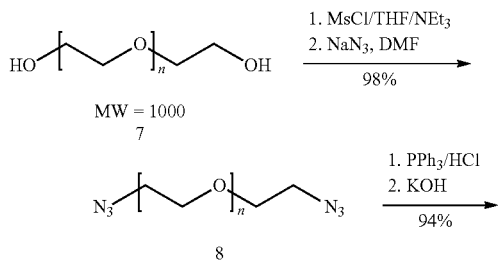

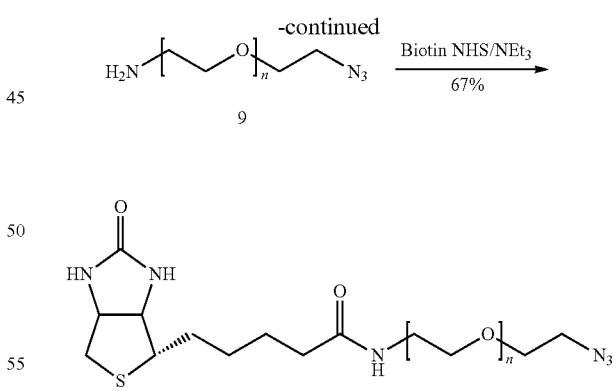

After the synthesis of the biotinylated probe, B-YL, the probe can be evaluated with a commercially available firefly luciferase. B-YL displayed bioluminescence with a maximum emission at 590 nm and can be oxidized by commercial luciferase to emit bioluminescence photons (FIG. S1). The mechanism for generating bioluminescence is shown in Scheme 2.

Scheme 2. Production of bioluminescence from probe B-YL (1).

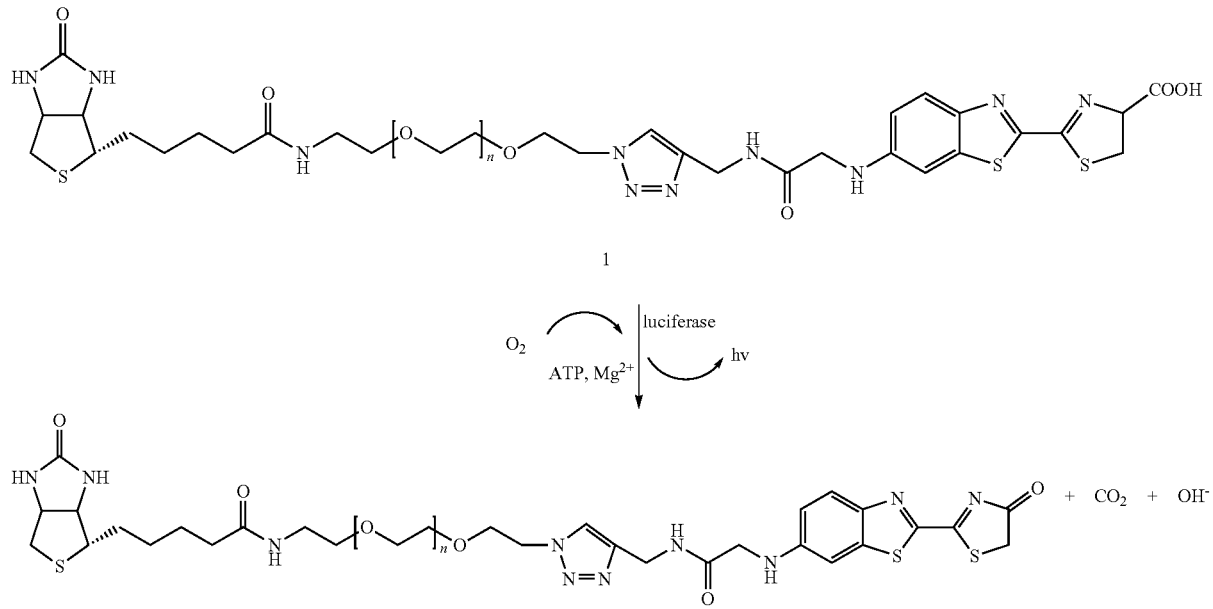

The B-YL substrate can be incubated with the brain cancer cell line U87-luc, which was derived from the parental brain cancer cell line U87 after stable transfection with a luciferase gene. As shown in FIG. 1a, B-YL applied to cancer cells without luciferase, parental U87, did not reveal bioluminescence activity regardless of the number of cells. However, as shown in FIG. 1b, when there were at least 7,500 U87-luc cells or more in a well, bioluminescence signal was detected by using B-YL. B-YL clearly adsorbed across the cell membrane and was oxidized by luciferase. Therefore, B-YL can be used for the detection of the cancer cells by bioluminescence.

Using classical avidin-biotin complex (ABC) formation, complexes can be made with a streptavidin or avidin core, which lacks any carbohydrate modification and had a near-neutral pH, and biotinylated ligands in the presence or absence of free biotin (B). The complex EGF-B-SA-B-YL (SA/B-YL/B-EGF=1/3/1, molar ratio) shown below (and also referred to herein as formula III) is a targeting complex which can be used as an active imaging agent for the detection of brain cancer cells:

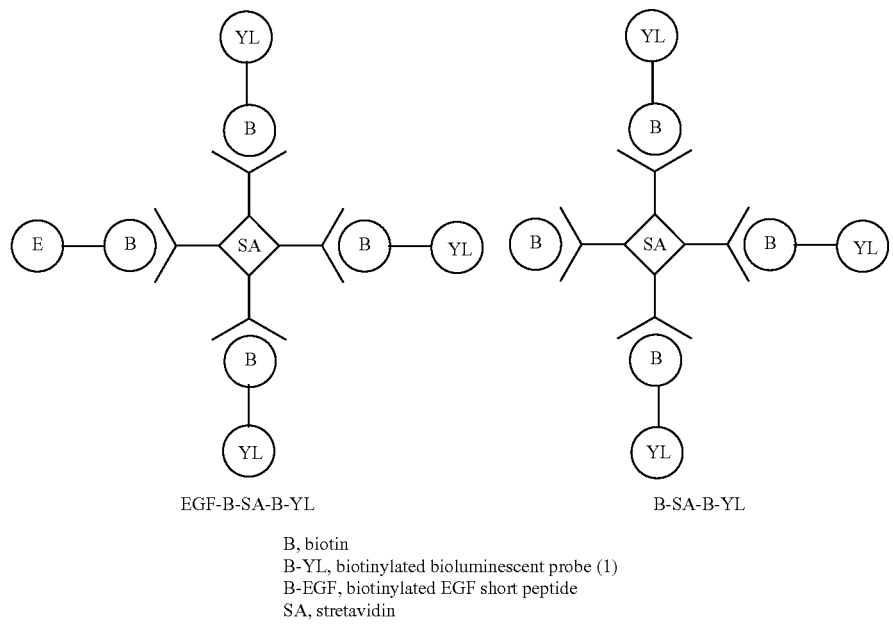

EGF-B-SA-B-YL           B-SA-B-YL

B, biotin
B-YL, biotinylated bioluminescent probe (1)
B-EGF, biotinylated EGF short peptide
SA, stretavidin Complex EGF-B-SA-B-YL possesses targeting functionality because it has an EGF short peptide. The complex B-SA-B-YL (SA/B-YL/B=1/3/1, molar ratio) shown above is a control complex with no targeting ability (no conjugated EGF short peptide).

Figure 2:
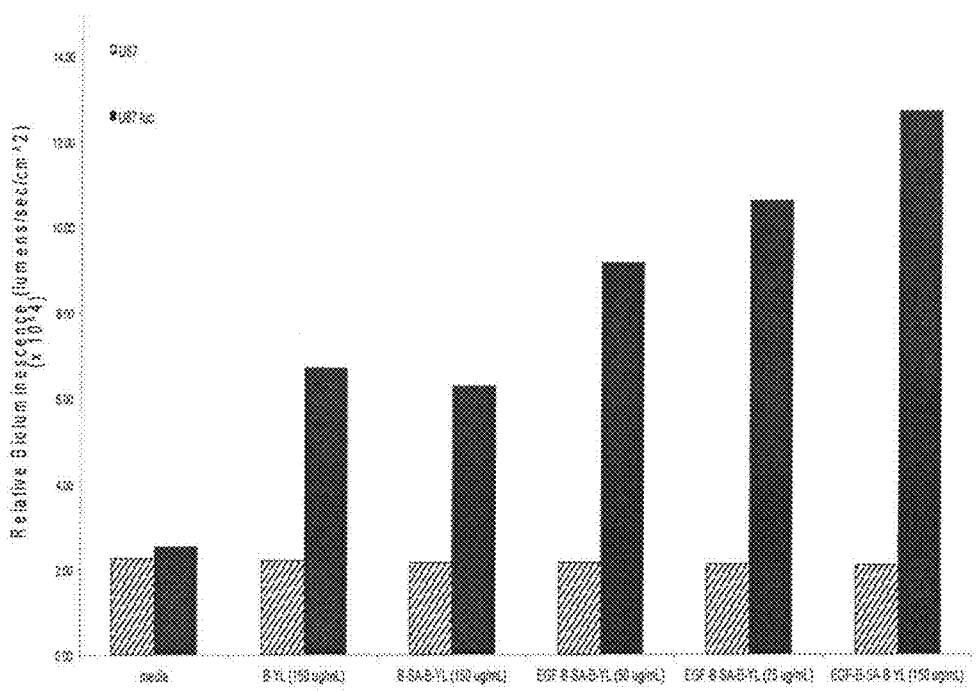
FIG. 2 shows relative bioluminescence intensities of imaging of brain cancer cells U87 (gray hatch bars) and brain tumor cell lines transfected with luciferase U87-luc (black bars) after treating with free B-YL substrate (150 μg/mL), B-SA-B-YL (complex of B-YL substrate with streptavidin and free biotin, 150 μg/mL, untargeted) and EGF-B-SA-B-YL (complex of B-YL substrate with streptavidin and biotinylated EGF short peptide, 50, 75 and 150 μg/m L, respectively, targeted).

The EGF-B-SA-B-YL complex can be tested for the ability to target and image brain cancer cell lines that overexpress the biomarker EGFR using bioluminescence in vitro. U87 (gray hatch bars) and U87-luc (black bars) cells can be treated with free B-YL (150 μg/m L), untargeted B-SA-B-YL complex (150 μg/mL) or EGFR-targeted EGF-B-SA-B-YL complex (50-150 □g/mL). Bioluminescence were detected immediately. As shown in FIG. 2, increasing concentrations of EGF-B-SA-B-YL complex actively accumulated into both U87 and U87-luc cells due to the presence of the EGF short peptide. However, only cells with luciferase were able to convert the EGF-B-SA-B-YL complex into detectable photons. Bioluminescence intensity depends directly on the amount of administered complex. Signal intensity increased linearly with increasing concentrations of the EGF-B-SA-B-YL complex. Cells without luciferase (U87) did not oxidize the EGF-B-SA-B-YL complex and release photons.

Untargeted B-SA-B-YL passively accumulated within the brain cancer cells. Luciferase activity for untargeted B-SA-B-YL was comparable to that of adsorbed free B-YL at the same concentration in U87-luc cells. The bioluminescence signal intensity from the targeted EGF-B-SA-B-YL complex is 2.5-fold higher than that of the untargeted B-SA-B-YL complex, suggesting the complex EGF-B-SA-B-YL could image cancer cells U87-luc much better than complexed B-SA-B-YL. Neither of the complexes (B-SA-B-YL or EGF-B-SA-B-YL) nor free B-YL were converted to bioluminescence photons by U87 cancer cells because they do not have luciferase activity.

Figure 3:
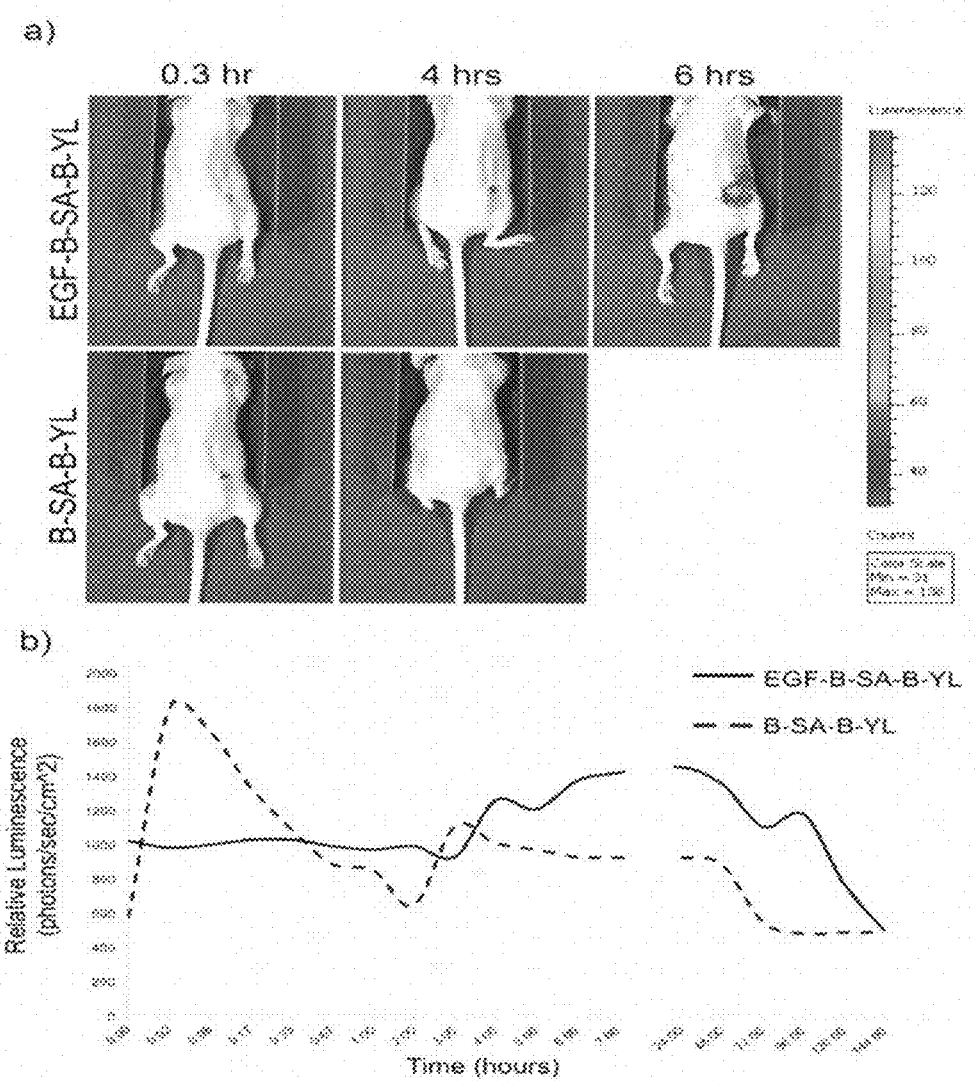
FIG. 3 shows in vivo imaging of xenograft U87-luc brain tumors in mice using targeted complexes EGF-B-SA-B-YL (150 μg/mL) and B-SA-B-YL (150 μg/mL). (a) Bioluminescence signals from mice using complex EGF-B-SA-B-YL (top) and B-SA-B-YL (bottom). (b) Bioluminescence signal intensities based on time using complexes EGF-B-SA-B-YL (solid line) and B-SA-B-YL (broken line).

The targeted EGF-B-SA-B-YL complex or untargeted B-SA-B-YL complex can be administered to mice with subcutaneously implanted xenograft brain tumors derived from U87-luc cancer cells (right flank) or U87 cancer cells (left flank) and evaluated for bioluminescence activity. In FIG. 3a, targeted EGF-B-SA-B-YL revealed increasing bioluminescence in the right flank tumor region (U87-luc) of a mouse from 0.3 h to 6 h. The signal was strong 6 h after injection of the complex. In contrast, administration of the untargeted B-SA-B-YL resulted in a weak bioluminescence signal after 0.3 h. The signal was completely gone after 4 h. The results suggest that the EGF-B-SA-B-YL complex is a suitable imaging agent for detection of luciferase activity within tumors.

Furthermore, in FIG. 3b, longitudinal imaging of mice injected with either targeted EGF-B-SA-B-YL complex (solid line) or untargeted B-SA-B-YL complex (dashed line), revealed that the signal from untargeted B-SA-B-YL complex peaked at 0.02 h after injection, suggesting that the B-SA-B-YL complex had an even shorter retention time than that reported for D-luciferin in mice (20-30 min). Both the B-SA-B-YL complex and D-luciferin do not have targeting function.

When the EGF-B-SA-B-YL complex was used, the maximum bioluminescence intensity was achieved at 24 h, suggesting the retention time for the EGF-B-SA-B-YL complex was very long. When the B-SA-B-YL complex was used, the maximum bioluminescence intensity was achieved at 0.02 h, there is 1200-fold increase in terms of retention time of bioluminescence from EGF-B-SA-B-YL. Furthermore, it took approximately 3 h to accumulate EGF-B-SA-B-YL within the tumor and EGF-B-SA-B-YL can be retained and bioluminescence will last 24 h. The signal of bioluminescence finally disappeared after the $6^{th}$ day, suggesting that the bioluminescence from EGF-B-SA-B-YL complex had very long retention time. Retention time range is day 1 to day 5 with at least half of maximum bioluminescence intensity; the upper limit is 5 days with at least half of maximum bioluminescence intensity.

The invention will now be further described in the Examples below, which are intended as an illustration only and do not limit the scope of the invention.

EXAMPLES

All chemicals used were purchased from commercial sources and used without further purification. Firefly luciferase was also purchased (Sigma, MO). Flash chromatography was performed with silica (70-230 mesh) and monitored by thin layer chromatography (TLC) with silica plates. The $^1$H spectra were recorded on a 400 MHz instrument (Bruker, MA) with methanol-$d_4$, DMSO-$d_6$ and $CDCl_3$. The chemical shifts of protons are given in ppm relative to the signal of tetramethylsilane (TMS) as the internal standard. The purification of compound 1 was carried out using a high performance liquid chromatography (HPLC) instrument (Dionex Ultimate 3000; Thermo Scientific, MA). Luminescence spectroscopy measurement was performed using a SynergyMx (BioTek, VT). HRMS spectra were performed in a Mass Spectrometry Service Center (UC Riverside, Calif.).

Example 1

Poly(ethylene glycol)$_{23}$-diazide (8)

PEG-1000 (20 g, 0.02 mol) was dehydrated by refluxing with toluene (100 mL), which was distilled out after reflux. After cooling, the PEG-1000 was dissolved in THF (150 mL). To the solution, was added mesyl chloride (4.88 mL) in one portion and triethylamine (9.16 mL) in TI-IF (80 mL) dropwise over 30 min at 0° C. The mixture was stirred for 1 h at 0° C. and 3 h at room temperature, affording PEG dimesylate solution in THF. A small amount of solution was extracted with dichloromethane, washed with water and dried over $Na_2SO_4$. After concentration, the residue was used for characterization. $^1$H NMR (400 MHz, $CDCl_3$, ppm) δ 3.11 (s, J=5.2 Hz, 4H), 3.65 (s, 85H).

To the solution of PEG dimesylate in THF, was added sodium bicarbonate (5%, 44 mL) and sodium azide (5.2 g). The resultant mixture was concentrated to 250 mL, stirred at room temperature overnight, and refluxed for 5 h. After cooling, the mixture was extracted with dichloromethane (3×100 mL). The resultant organic layer was dried over $MgSO_4$ and concentrated to PEG diazide (20.7 g, 98%). The product was used for next step without further purification. $^1$H NMR (400 MHz, $CDCl_3$, ppm) δ 3.40 (t, 6H), 3.67 (s, 81H), 3.78-3.80 (m, 4H), 4.40-4.41 (m, 4H). Mass calculated for $C_{44}H_{88}N_6O_{21}^+$ (M+H$^+$) 1037, found 1032.

Example 2

Amino-poly(ethylene glycol)$_{23}$-azide (9)

To the PEG diazide (8, 10.7 g, 10.2 mmol) solution in EtOAc (60 mL), was added HCl (1N, 12 mL), and triphenylphosphine (2.67 g, 10.2 mmol). The mixture was stirred for 12 h at room temperature. Water (12 mL) was added into the reaction mixture and the mixture was extracted with EtOAc (2×50 mL) to remove unreacted PEG diazide. Solid potassium hydroxide (9.28 g) was added at 0° C. The mixture was then extracted with $CH_2Cl_2$ (3×50 mL). The organic layer was washed with brine, dried over $Na_2SO_4$ and concentrated to 9.8 g of amino containing PEG compounds (azido PEG monoamine and PEG diamine) in 94% yield. $^1$H NMR (400 MHz, $CD_3OD$, ppm) δ 2.80-2.82 (m, 2H), 3.39-3.42 (m, 2H), 3.55 (m, 2H), 3.63 (s, 86H). Mass calculated for $C_{44}H_{90}N_4O_{21}^+$ (M+H$^+$) 1011, found 1012.

Example 3

N-(Azido-poly (ethylene glycol)$_{23}$)-hexahydro-2-oxo-(3aS,4S,6aR)-1H-thieno[3,4-d]imidazole-4-pentanamide (5)

To the above amino containing PEG compounds 9 (9.8 g) in DMF (70 mL) and Net$_3$ (2.76 mL), was added biotin NHS (3.93 g, 11.48 mmol). After stirring overnight at room temperature, the reaction mixture was concentrated, dissolved in $CH_2Cl_2$, centrifuged to a clear solution and purified with column chromatography (silica gel, dichloromethane-dichloromethane/acetone/methanol (2:7:1)-dichloromethane/methanol (9:1)) to yield product 5 (67%). $^1$H-NMR (400 MHz, CDCl$_3$, ppm) δ 1.45-1.49 (m, 2H), 1.70-1.75 (m, 4H), 2.28 (t, J=7.9 Hz, 2H), 2.72-2.79 (m, 1H), 2.92 (dd, J=12.8, 4.8 Hz, 1H), 3.17-3.18 (m, 1H), 3.41 (t, J=5.0 Hz, 2H), 3.59 (t, J=5.0 Hz, 2H), 3.65-3.75 (m, 75H), 4.34-4.37 (m, 1H), 4.53-4.56 (m, 1H), 6.21 (s, 1H), 6.76 (s, 1H). Mass calculated for $C_{54}H_{104}N_6O_{23}Sna^+$ (n=22, M+Na$^+$) 1259.677, found 1259.681.

Example 4

N'-Propargyl N"-(2-cyano-6-benzothiazolyl)-glycinamide (4)

To a solution of N-(2-cyano-6-benzothiazolyl)-glycine (2, 0.57 g, 2.6 mol) in tetrahydrofuran (100 mL) and acetonitrile (70 mL), were added propargyl amine (3, 0.33 mL, 5.2 mmol), 1-ethyl-3-(3-dimethylaminopropyl)carbodiimide (EDC) (0.996 g, 5.2 mmol) and 1-hydroxybenzotriazole (HOBt) (0.8 g). The mixture was stirred overnight, concentrated in vacuo, dissolved in dichloromethane (50 mL), washed with saturated sodium bicarbonate (50 mL), and dried over magnesium sulfate. After concentration, residue was purified with column chromatography (silica gel, hexane, ethyl acetate, then acetone) to yield 0.59 g (88%) product 4. $^1$H NMR (400 MHz, CD$_3$COCD$_3$, ppm) δ 2.65 (t, J=2.4 Hz, 1H), 3.97 (d, J=5.6 Hz, 2H), 4.05 (dd, J=5.6, 2.5 Hz, 2H), 6.30 (s, 1H), 7.17 (m, 1H), 7.19 (s, 1H), 7.79 (s, 1H), 7.96 (d, J=8.6 Hz, 1H). Mass calculated for $C_{13}H_{11}N_4OS^+$ (M+H$^+$) 271.065, found 271.064.

Example 5

N-(5-(N"-(2-Cyano-6-benzothiazolyl)-glycinamidomethyl)-1H-1,2,3-triazolyl-poly(ethylene glycol)$_{23}$)-hexahydro-2-oxo-(3aS,4S,6aR)-1H-thieno[3,4-d]imidazole-4-pentanamide (6)

To a solution of 4 (0.185 g, 0.72 mmol) and N-(azido-poly (ethylene glycol)$_{23}$)-hexahydro-2-oxo-(3aS,4S,6aR)-1H-thieno[3,4-d]imidazole-4-pentanamide (5, 0.45 g, 0.36 mmol) in DMF (4.0 mL), were added tris[(1-benzyl-1H-1, 2,3-triazol-4-yl)methyl]amine (TBTA, 3.3 mg) and Cu(CH$_3$CN)$_2$PF$_6$ (29.8 mg) under $N_2$ stream at room temperature. The resultant mixture was stirred at 40'C overnight. After evaporation of solvent in high vacuum, the residue was purified with column chromatography (silica gel, dichloromethane-dichloromethane/methanol (88/12 (v/v))) to yield 0.402 g (74%) product 6. $^1$H NMR (400 MHz, CD$_3$OD, ppm) δ 1.47-1.48 (m, 2H), 1.63-1.74 (m, 4H), 2.27 (t, J=7.5 Hz, 2H), 2.75 (d, J=12.8 Hz, 1H), 2.98 (dd, J=12.8, 2.5 Hz, 1H), 3.22-3.24 (m, 1H), 3.37-3.39 (m, 2H), 3.60-3.65 (m, 82H), 3.86 (d, J=5.0 Hz, 2H), 3.96 (s, 2H), 4.31-4.35 (m, 1H), 4.51-4.60 (m, 5H), 7.08-7.10 (min, 2H), 7.92-7.94 (m, 2H), 8.02 (s, 1H). Mass calculated for $C_{63}H_{107}N_{10}O_{22}S_2$ (n=18, M+H$^+$) 1419.700, found 1419.700.

Example 6

6-(3-N—{N-[5-(Hexahydro-2-oxo-1H-thieno[3,4-d] imidazol-4-yl)-1-oxopentyl]-, [3aS-(3aα,4β, 6aα)]}-aminoethyl-poly(ethylene glycol)$_{21}$-oxyethyl-1H-1, 2,3-triazol-5-yl-methylamino-oxomethyl-amino)-2-benzothiazolyl]-4,5-dihydro-,(4S)-4-thiazolecarboxylic acid (1)

To a solution of compound 6 (15.07 mg, 0.9 mmol) in methanol (6 mL), was added a solution of D-cysteine (9.31 mg) in water (1.8 mL). The mixture was titrated with potassium carbonate (0.05 M) to pH 8. The mixture was then stirred for 10 min at room temperature. After concentration with $N_2$ stream, the residue was purified with high performance liquid chromatography (HPLC) using a reverse phase column and 20-100% acetonitrile in a gradient condition, affording probe 1 (10.1 mg, 67% yield). $^1$H NMR (400 MHz, CD$_3$OD, ppm) δ 1.46-1.47 (m, 2H), 1.65-1.69 (m, 4H), 2.24 (m, 2H), 2.74 (d, J=12.4 Hz, 1H), 2.93-2.97 (m, 1H), 3.22 (m, 1H), 3.33-3.66 (m, 84H), 3.82 (s, 2H), 3.91 (s, 2H), 4.10-4.12 (m, 1H), 4.33 (s, 1H), 4.52 (s, 4H), 6.90-6.99 (m, 2 Hi), 7.76-7.60 (m, 2H). Ultra-violet maximum absorption was at 365 nm and maximum fluorescence emission was at 515 nm in Leibovitz's L-15 medium (pH 7.8). Mass calculated for $C_{66}H_{112}N_{11}O_{24}S_3$ (n=18. M+1H$^+$) 1538.704, found 1538.706.

Example 7

Measurement of Bioluminescence Spectrum of Probe B-YL (1)

In a well of 96 quartz plate (500 μl), HEPES buffer (30 mM) solution (400 μl, pH=7.7) containing MgSO$_4$ (5.0 mM), ATP (2.6 mM), DTT (3.5 mM), CoA (1.5 mM) and commercially available firefly luciferase (40 μg/ml), was prepared. The probe B-YL was then added and mixed to a final concentration (32 μM). Bioluminescence spectrum of B-YL was then taken immediately with instrument SynergyMx (BioTek, VT).

Example 8

Formation of B-YL Complexes

Preparation of a Complex of Streptavidin with B-YL and Free Biotin (B-SA-B-YL, 1-3-1 Molar Ratio)

Streptavidin (189 μM, stock solution A) was prepared by dissolving streptavidin solid (10.0 mg) in PBS buffer (1.0 mL, pH 7.4). Biotin was prepared in dimethyl sulfoxide (DMSO) (1.0 mM). Biotin (1.0 mM, 0.189 mL) and B-YL (6.5 mM, 0.0852 mL) were added to DMSO (0.20 mL), resulting in solution B after mixing. Solution A was then mixed with solution B evenly. The resulting mixture was incubated at room temperature for 30 minutes. The mixture was then transferred into a membrane filter cassette (20 kDa cut-off) and dialyzed in PBS buffer (1000 mL) overnight. The B-SA-B-YL solution was removed from the cassette. Concentration was measured by UV spectroscopy (76.4 μM, 353 μg/mL).

Preparation of a Complex of Streptavidin with B-YL and EGF Peptide (EGF-B-SA-B-YL, 1-3-1 Molar Ratio)

Biotinylated EGF short peptide (B-Tyr-His-Trp-Tyr-Gly-Tyr-Thr-Pro-Gln-Asn-Val-Ile-$NH_2$) was prepared in dimethyl sulfoxide (DMSO) (1.0 mM). Biotinylated EGF short peptide (1.0 mM, 0.189 mL) and B-YL (6.5 mM, 0.0852 mL) were added to DMSO (0.20 mL), resulting in a solution B after mixing evenly. Solution A was then mixed with B evenly. The resulting mixture was incubated at room temperature for 30 minutes. The mixture was then transferred into a membrane filter (cassette, 20 KDa cut-off) and dialyzed in PBS buffer (1000 mL) overnight. The EGF-B-SA-B-YL solution was drawn out of the membrane filter. Concentration was measured by UV spectroscopy (111 μM, 512 μg/mL).

Example 9

Measuring Bioluminescence in Brain Cancer Cell Lines

U87 cells either expressing luciferase (+luc) or not (−luc) were subcutaneously implanted in the flanks of mice and grown to 1 cm in diameter (approximately 21 days) as per IUCAC approved protocols. Targeted EGF-B-SA-B-YL complex (150 g/mL) or untargeted B-SA-B-YL complex (150 μg/mL) was then administered to mice with subcutaneously implanted xenograft brain tumors derived from U87-luc cancer cells (right flank) or U87 cancer cells (left flank) and evaluated for bioluminescence activity. The complex can be administered either intratumorally, intraperitoneally, or intravenously.

Thus, as shown in the Examples above, a novel biotinylated probe B-YL has been synthesized. B-YL possesses a biotin unit for binding to streptavidin or avidin, a PEG linker for improving cell penetration and a luciferin unit for bioluminescence triggered by luciferase. After synthesis, the B-YL was tested and found to be a substrate of firefly luciferase. B-YL was then used to form complexes with streptavidin together with biotinylated EGF short peptide to create targeted and untargeted complexes. The EGF-B-SA-B-YL complex produced stronger bioluminescent signal in brain cancer cell lines with an encoded luciferase gene (U87-luc). By using the EGF-B-SA-B-YL complex, bioluminescence signal in xenograft brain tumors in mice was also detected. More importantly, the bioluminescence in the xenografted mouse lasted several days, suggesting that the targeted complex could be a long lasting bioluminescent agent for brain cancer imaging in vivo. This imaging agent could find applications in brain cancer detection and surgery in the brain using bioluminescence, when tumors are removed and the surgery lasts several hours.

The invention will be further described, without limitation, by the following numbered paragraphs:

1. A bioluminescent probe of formula I (B-YL):

I 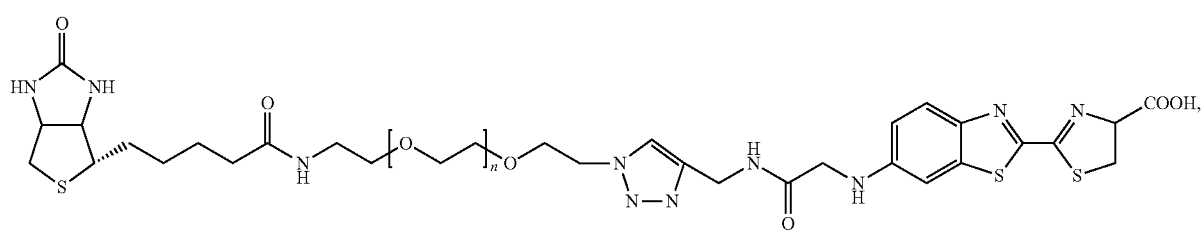 wherein n is 10 to 200,
or a derivative thereof.

2. The bioluminescent probe according to paragraph 1, wherein n is 10 to 150.

3. The bioluminescent probe according to paragraph 1, wherein n 10 to 100.

4. The bioluminescent probe according to paragraph 1, wherein n is 10 to 50.

5. The bioluminescent probe according to paragraph 1, wherein n is 11, 23, 45 or 114.

6. The bioluminescent probe according to paragraph 1, wherein n is 23.

7. A compound of formula II:

II 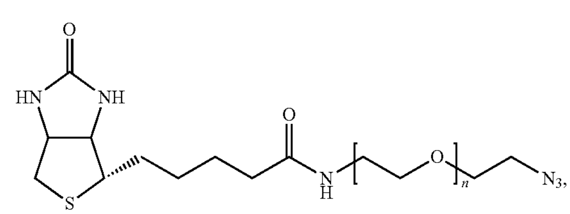 wherein n is 10 to 200,
or a derivative thereof.

8. The bioluminescent probe according to paragraph 1, wherein said probe has a maximum ultraviolet absorbance at 515 nm.

9. The bioluminescent probe according to paragraph 1, wherein said probe has a luminescence emission at 590 nm.

10. A complex of formula III:

(III)

wherein:
B is biotin;
B-YL is the biotinylated bioluminescent probe of paragraph 1;
B-E is a biotinylated EGF short peptide; and
SA is streptavidin or avidin.

11. A method for detecting cancer cells in a sample, comprising the step of:
contacting the complex of formula III according to paragraph 10 with cancer cells in said sample;
introducing B-YL to said sample; and
detecting an optical signal from the reaction of said complex of formula III with luciferase.

12. An assay method for detecting a cancer cell in a sample, comprising the steps of:
causing the bioluminescent probe of formula I according to paragraph 1 to bind to a cancer cell in said sample so as to form a conjugate;
administering an amount of luciferase to said sample; and
detecting the presence of cancer cells in said sample.

13. A kit for determining the presence of cancer in a patient sample, comprising a probe of formula I:

wherein n is 10 to 200, or a complex of formula II:

(II)

wherein:
B is biotin;
B-YL is the biotinylated bioluminescent probe of paragraph 1;
B-E is a biotinylated EGF short peptide; and
SA is streptavidin or avidin.

14. The kit according to paragraph 13, further comprising luciferase.

15. The kit according to paragraph 13, further comprising instructions for use.

It is to be understood that the invention is not limited to the particular embodiments of the invention described above, as variations of the particular embodiments may be made and still fall within the scope of the appended claims.

What is claimed is:

1. A bioluminescent probe of formula I (B-YL):

I

I

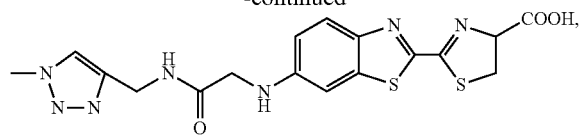

wherein n is 10 to 200,
or a derivative thereof.

2. The bioluminescent probe according to claim 1, wherein n is 10 to 150.

3. The bioluminescent probe according to claim 1, wherein n 10 to 100.

4. The bioluminescent probe according to claim 1, wherein n is 10 to 50.

5. The bioluminescent probe according to claim 1, wherein n is 11, 23, 45 or 114.

6. The bioluminescent probe according to claim 1, wherein n is 23.

7. The bioluminescent probe according to claim 1, wherein said probe has a maximum ultraviolet absorbance at 515 nm.

8. The bioluminescent probe according to claim 1, wherein said probe has a luminescence emission at 590 nm.

* * * * *